(12) United States Patent
Shin (10) Patent No.: US 11,399,700 B2
(45) Date of Patent: Aug. 2, 2022

(54) PROCESSING DEVICE, ENDOSCOPE, ENDOSCOPE SYSTEM, IMAGE PROCESSING METHOD, AND COMPUTER-READABLE RECORDING MEDIUM FOR CORRECTING A DEFECTIVE PIXEL

(71) Applicant: OLYMPUS CORPORATION, Tokyo (JP)

(72) Inventor: Hidetoshi Shin, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 309 days.

(21) Appl. No.: 16/838,120

(22) Filed: Apr. 2, 2020

(65) Prior Publication Data
US 2020/0229678 A1     Jul. 23, 2020

Related U.S. Application Data (63) Continuation of application No. PCT/JP2018/027977, filed on Jul. 25, 2018.

(30) Foreign Application Priority Data

Oct. 5, 2017   (JP) .............................. JP2017-195392

(51) Int. Cl.
    *A61B 1/00*     (2006.01)
    *A61B 1/05*     (2006.01)
    (Continued)

(52) U.S. Cl.
    CPC ...... *A61B 1/00009* (2013.01); *A61B 1/00006* (2013.01); *A61B 1/0051* (2013.01);
    (Continued)

(58) Field of Classification Search
    CPC .............................................. H04N 2005/2255
    See application file for complete search history.

(56) References Cited

U.S. PATENT DOCUMENTS

2009/0310849 A1 * 12/2009 Katou .................. H04N 5/3675
                                                         382/149
2010/0328511 A1 * 12/2010 Tashiro .............. H04N 5/37457
                                                         348/301
(Continued)

FOREIGN PATENT DOCUMENTS

JP       2013-211785 A     10/2013
JP       2013219665 A   *  10/2013
(Continued)

OTHER PUBLICATIONS

International Search Report dated Oct. 2, 2018 issued in PCT/JP2018/027977.

*Primary Examiner* — John P Leubecker
(74) *Attorney, Agent, or Firm* — Scully, Scott, Murphy & Presser, P.C.

(57) ABSTRACT

A processing device includes: a processor including hardware, the processor being configured to acquire image data; determine, for each pixel of an image corresponding to the acquired image data, whether a pixel value of the pixel is equal to or less than a preset threshold as a dark level; accumulate, for a predetermined number of frames, the pixel value that has been determined to be equal to or less than the preset threshold and positional information regarding a position of the pixel whose pixel value has been determined to be equal to or less than the preset threshold, on the image sensor; calculate a statistical value of the accumulated pixel values for each pixel; determine, for each pixel, whether the statistical value falls outside a preset range; and correct a (Continued)

pixel value of the pixel whose statistical value has been determined to fall outside the preset range.

10 Claims, 3 Drawing Sheets

(51) Int. Cl.
    *H04N 5/367*     (2011.01)
    *A61B 1/005*     (2006.01)
    *A61B 1/06*     (2006.01)

(52) U.S. Cl.
    CPC ............ *A61B 1/00163* (2013.01); *A61B 1/05* (2013.01); *A61B 1/0661* (2013.01); *H04N 5/367* (2013.01); *H04N 5/3675* (2013.01)

(56) References Cited

U.S. PATENT DOCUMENTS

2013/0314516 A1*   11/2013   Uchihara ............ H04N 5/3675
                                                                               348/65
2016/0241800 A1     8/2016   Shin
2017/0302867 A1    10/2017   Ichikawa et al.

FOREIGN PATENT DOCUMENTS

JP           2014-216775 A     11/2014
WO    WO 2015/098235 A1    7/2015
WO    WO 2016/117034 A1    7/2016

\* cited by examiner

PROCESSING DEVICE, ENDOSCOPE, ENDOSCOPE SYSTEM, IMAGE PROCESSING METHOD, AND COMPUTER-READABLE RECORDING MEDIUM FOR CORRECTING A DEFECTIVE PIXEL

CROSS-REFERENCE TO RELATED APPLICATION

This application is a continuation of PCT International Application No. PCT/JP2018/027977 filed on Jul. 25, 2018, which designates the United States, incorporated herein by reference, and which claims the benefit of priority from Japanese Patent Application No. 2017-195392, filed on Oct. 5, 2017, incorporated herein by reference.

BACKGROUND

1. Technical Field

The present disclosure relates to a processing device connected to an endoscope that is to be inserted into a living body of a subject to capture an image of an inside of the living body, and to an endoscope, an endoscope system, an image processing method, and a computer-readable recording medium.

2. Related Art

In the related art, a solid state image sensor, such as a charge coupled device (CCD) or a complementary metal oxide semiconductor (CMOS), includes a plurality of pixels that receives light and performs photoelectric conversion to output electric signals. It is known that a defective pixel is present in such solid state image sensor, the defective pixel having no correlation with the amount of received light and outputting abnormal electric signals. Types of the defective pixels include regular defective pixels and flickering defective pixels, where the regular defective pixels always output abnormal electric signals due to, for example, dust on a light receiving surface or a crystal defect in the sensor, and the flickering defective pixels, which occur as solid state image sensors are made smaller, irregularly output abnormal electric signals due to a random telegraph signal (RTS) noise generated by a disturbed electric current attributed to trapping of electrons moving in a MOS transistor into the trap level present in a gate insulating film.

A flickering defective pixel appears on a captured image as an image noise irregularly generated when video images are being taken. According to one known technique for removing such image noise, a solid state image sensor is caused to capture images a plurality of times with the image sensor shielded from light, a flickering defective pixel is detected from a plurality of the captured images, and an electric signal corresponding to the detected flickering defective pixels is corrected (see JP 2013-211785 A).

SUMMARY

In some embodiments, a processing device includes: a processor including hardware, the processor being configured to acquire image data generated by an image sensor, determine, for each pixel of an image corresponding to the acquired image data, whether a pixel value of the pixel is equal to or less than a preset threshold as a dark level, accumulate, for a predetermined number of frames, the pixel value that has been determined to be equal to or less than the preset threshold and positional information regarding a position of the pixel whose pixel value has been determined to be equal to or less than the preset threshold, on the image sensor, calculate a statistical value of the accumulated pixel values for each pixel, determine, for each pixel, whether the statistical value falls outside a preset range, and correct a pixel value of the pixel whose statistical value has been determined to fall outside the preset range.

In some embodiments, an endoscope includes: an image sensor configured to capture an image of a subject to generate image data; and a processor including hardware, the processor being configured to determine, for each pixel of an image corresponding to the image data generated by the image sensor, whether a pixel value of the pixel is equal to or less than a preset threshold as a dark level, every time a determination of the pixel value is performed, accumulate, for a predetermined number of frames, the pixel value that has been determined to be equal to or less than the preset threshold and positional information regarding a position of the pixel whose pixel value has been determined to be equal to or less than the preset threshold, on the image sensor, calculate a statistical value of the accumulated pixel values for each pixel, determine, for each pixel, whether the statistical value falls outside a preset range, and correct a pixel value of the pixel whose statistical value has been determined to fall outside the preset range.

In some embodiments, an endoscope system includes: an endoscope comprising an image sensor configured to capture an image of a subject to generate image data; a processing device configured to perform image processing on the image data; and a processor including hardware, the processor being configured to determine, for each pixel of an image corresponding to the image data generated by the image sensor, whether a pixel value of the pixel is equal to or less than a preset threshold as a dark level, every time a determination of the pixel value is performed, accumulate, for a predetermined number of frames, the pixel value that has been determined to be equal to or less than the preset threshold and positional information regarding a position of the pixel whose pixel value has been determined to be equal to or less than the preset threshold, on the image sensor, calculate a statistical value of the accumulated pixel values for each pixel, determine, for each pixel, whether the statistical value falls outside a preset range, and correct a pixel value of the pixel whose statistical value has been determined to fall outside the preset range.

In some embodiments, an image processing method includes: acquiring image data generated by an image sensor; determining, for each pixel of an image corresponding to the acquired image data, whether a pixel value of the pixel is equal to or less than a preset threshold as a dark level; every time a determination of the pixel value is performed, accumulating, for a predetermined number of frames, the pixel value that has been determined to be equal to or less than the preset threshold and positional information regarding a position of the pixel whose pixel value has been determined to be equal to or less than the preset threshold, on the image sensor; calculating a statistical value of the accumulated pixel values for each pixel; determining, for each pixel, whether the statistical value falls outside a preset range; and correcting a pixel value of the pixel whose statistical value has been determined to fall outside the preset range.

In some embodiments, provided is a non-transitory computer-readable recording medium with an executable program stored thereon. The program causes a processing device to execute: acquiring image data generated by an image sensor; determining, for each pixel of an image corresponding to the acquired image data, whether a pixel value of the pixel is equal to or less than a preset threshold as a dark level; every time a determination of the pixel value is performed, accumulating, for a predetermined number of frames, the pixel value that has been determined to be equal to or less than the preset threshold and positional information regarding a position of the pixel whose pixel value has been determined to be equal to or less than the preset threshold, on the image sensor; calculating a statistical value of the accumulated pixel value for each pixel; determining, for each pixel, whether the statistical value falls outside a preset range; and correcting a pixel value of the pixel whose statistical value has been determined to fall outside the preset range.

The above and other features, advantages and technical and industrial significance of this disclosure will be better understood by reading the following detailed description of presently preferred embodiments of the disclosure, when considered in connection with the accompanying drawings.

DETAILED DESCRIPTION

The following describes a mode for carrying out the present disclosure (hereinafter called an "embodiment") taking as an example a medical endoscope system configured to capture and display an image of a body cavity of a subject such as a patient. The present disclosure is not limited to the embodiment. In addition, the same elements are given the same reference signs throughout descriptions of the drawings. Furthermore, it should be noted that the drawings are schematic ones and the relationship between thickness and width of each member, the ratio among individual members, and the like are different from the actual relationship, ratio, and the like. Moreover, the drawings include portions in which dimensions and ratios are inconsistent among the drawings.

Configuration of Endoscope System

Figure 1:
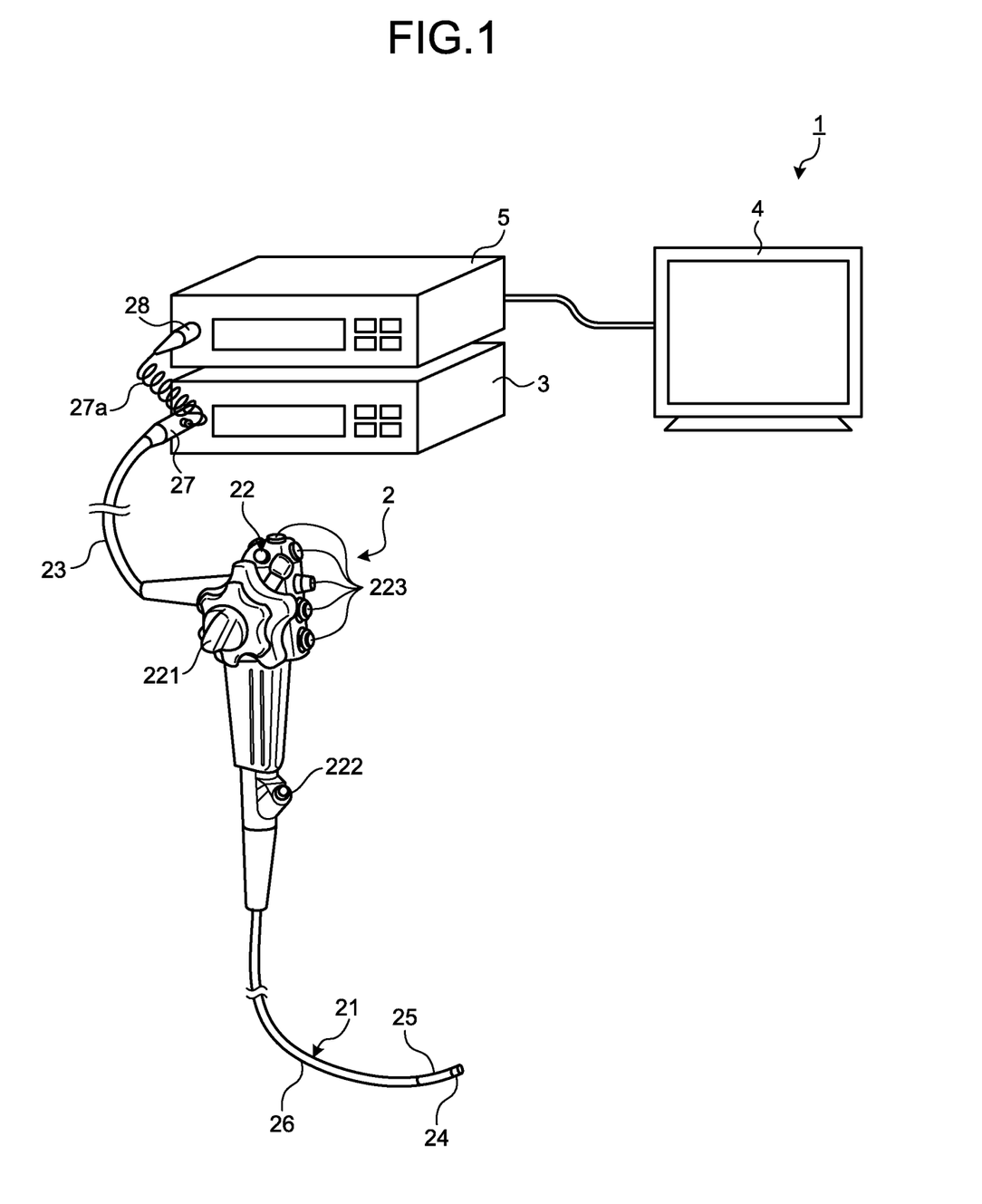
FIG. 1 is a schematic diagram illustrating a configuration of an endoscope system according to one embodiment of the present disclosure.
Figure 2:
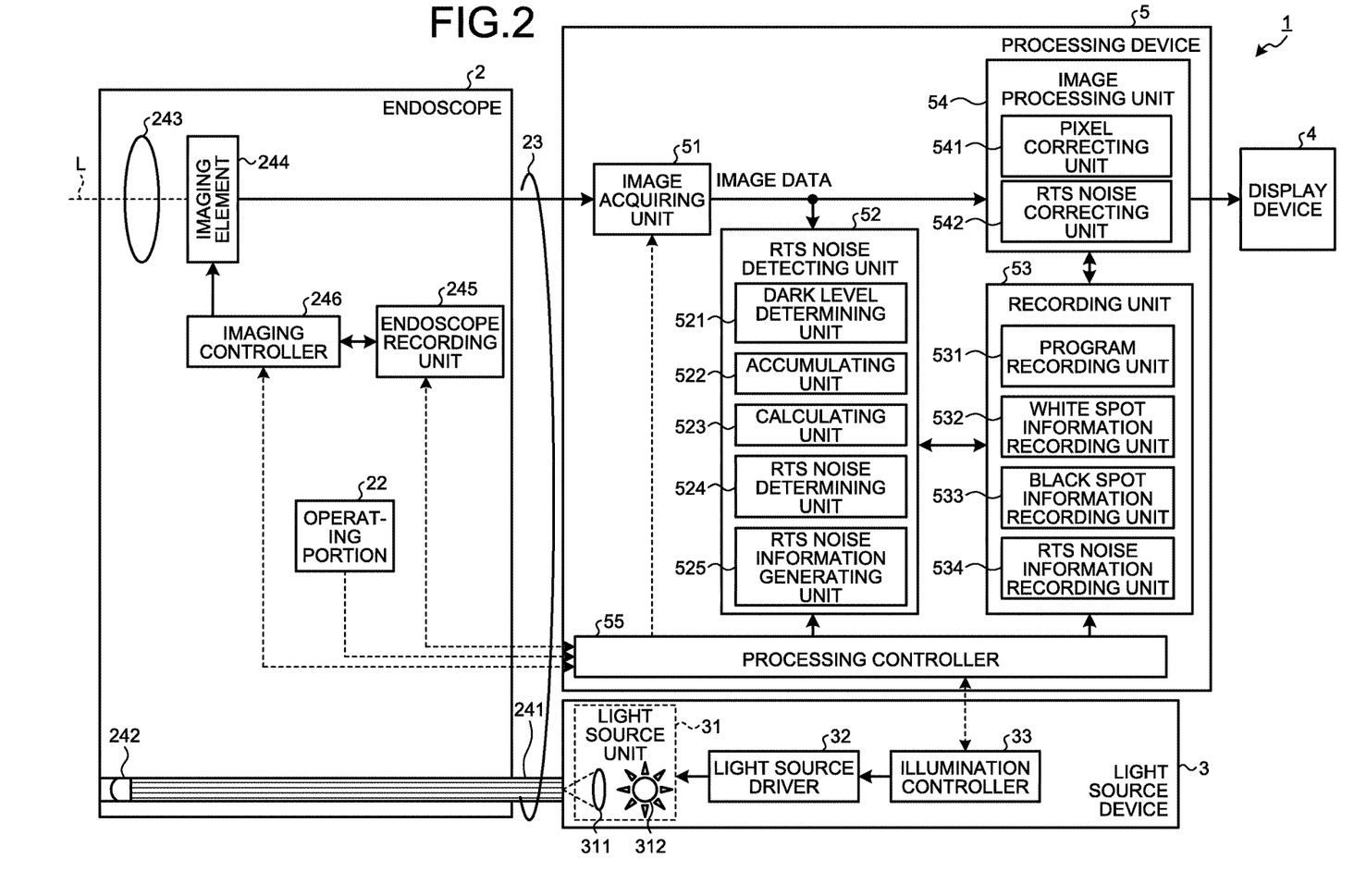
FIG. 2 is a block diagram illustrating a functional configuration of a major part of the endoscope system according to one embodiment of the present disclosure.

FIG. 1 is a schematic diagram illustrating a configuration of an endoscope system according to one embodiment of the present disclosure. FIG. 2 is a block diagram illustrating a functional configuration of a major part of the endoscope system according to one embodiment of the present disclosure.

An endoscope system 1 illustrated in FIG. 1 includes an endoscope 2 (electronic scope) that captures an image of the inside of the body of a subject to generate image data (RAW data), a light source device 3 that generates illumination light for illuminating the subject from the distal end of the endoscope 2, a display device 4 that is capable of displaying an image corresponding to the image data obtained through imaging by the endoscope 2, and a processing device 5 (processor) that performs predetermined image processing on the image data obtained through imaging by the endoscope 2 and outputs the resulting data to the display device 4, while exerting centralized control over overall operations of the endoscope system 1.

Configuration of Endoscope

First, a configuration of the endoscope 2 is described below.

The endoscope 2 includes an insertion portion 21 that has flexibility and an elongated shape, an operating portion 22 that is connected to the proximal end side of the insertion portion 21 and receives inputs of various operation signals, and a universal cord 23 that extends in a direction different from the direction in which the insertion portion 21 extends from the operating portion 22, and contains various cables connected to the light source device 3 and the processing device 5.

The insertion portion 21 includes a distal end portion 24 containing an imaging element 244 described later, a bending portion 25 being bendable and configured with a plurality of bending pieces, and a flexible tube portion 26 having flexibility and an elongated shape and connected to the proximal end side of the bending portion 25.

The distal end portion 24 includes a light guide 241 that is made of glass fibers or the like to constitute a light guide path for the light emitted by the light source device 3, an illumination lens 242 disposed at an end of the light guide 241, an optical system 243 for collecting light, an imaging element 244 that is disposed at an image forming position for the optical system 243 and has a plurality of pixels two-dimensionally arranged, the pixels receiving the light collected by the optical system 243 and performing photoelectric conversion to convert the light into electric signals, an endoscope recording unit 245 that records various types of information regarding the endoscope 2, and an imaging controller 246 that controls the imaging element 244.

The optical system 243 is configured by using one or more lenses and, by moving along an optical axis L, changes the optical zoom to change the angle of view and changes the focal point.

The imaging element 244, which has a plurality of pixels two-dimensionally arranged, the pixels receiving light and performing photoelectric conversion to output electric signals, captures images of a subject (body cavity) at a predetermined frame rate and outputs image data (RAW data). Specifically, the imaging element 244 is configured by using an image sensor, such as a charge coupled device (CCD) or a complementary metal oxide semiconductor (CMOS), in which a plurality of pixels are arranged in a two-dimensional matrix, the pixels each having a photodiode that accumulates electric charges corresponding to the amount of light and an amplifier that amplifies the electric charges accumulated by the photodiode. The imaging element 244 outputs, as image data, an electric signal (a pixel value) generated by each pixel to the processing device 5.

The endoscope recording unit 245 records various types of information regarding the endoscope 2, including, for example, identification information for identifying the endoscope 2 and identification information for the imaging element 244. The endoscope recording unit 245 is configured by using a volatile memory or the like.

The imaging controller 246 controls operations of the imaging element 244 on the basis of instruction information input from the processing device 5. Specifically, the imaging controller 246 controls the frame rate for the imaging element 244 on the basis of instruction information input from the processing device 5. For example, the imaging controller 246 causes the imaging element 244 to output image data at 60 fps.

The operating portion 22 includes a bending knob 221 that causes the bending portion 25 to bend in vertical and horizontal directions, a treatment tool insertion portion 222 from which a treatment tool such as biological forceps, a laser scalpel, or a test probe is inserted into the body cavity, and a plurality of switches 223 serving as an operation input unit from which operation instruction signals for peripheral equipment such as an air supply unit, a water supply unit, and a gas supply unit in addition to the light source device 3 and the processing device 5 or pre-freeze signals indicating instructions that the imaging element 244 is to take still images are input. The treatment tool inserted from the treatment tool insertion portion 222 passes through a treatment tool channel (not illustrated) of the distal end portion 24 to come out of an opening (not illustrated).

The universal cord 23 contains at least the light guide 241 and a cable assembly in which one or more cables are put together. The cable assembly includes signal lines for transmitting signals between the endoscope 2 and either of the light source device 3 and the processing device 5, including, for example, a signal line for transmitting configuration data, a signal line for transmitting image data, and a signal line for transmitting drive timing signals for driving the imaging element 244. The universal cord 23 includes a connector unit 27 attachable and detachable to/from the light source device 3. A coil cable 27a being coiled extends from the connector unit 27, and a connector unit 28 attachable and detachable to/from the processing device 5 is disposed at the end of the extending coil cable 27a.

Configuration of Light Source Device

Next, a configuration of the light source device 3 is described below.

The light source device 3 includes a light source unit 31, a light source driver 32, and an illumination controller 33.

The light source unit 31 emits illumination light with which the subject is irradiated. The light source unit 31 includes a condenser lens 311 and a light source 312. The condenser lens 311, which is configured by using one or more lenses, collects the light emitted by the light source 312. The light source 312, which is configured by using a light emitting diode (LED), generates white light. Note that the light source 312 may be configured by using a red LED, a green LED, and a blue LED and employ simultaneous lighting by which the individual LEDs simultaneously emit light to generate white light, or may be configured by using a red LED, a green LED, and a blue LED and employ sequential lighting by which the individual colors are sequentially generated.

The light source driver 32 causes the light source 312 to intermittently generate white light by supplying an electric current to the light source 312 under the control of the illumination controller 33. The light generated by the light source 312 passes through the condenser lens 311 and the light guide 241 and is radiated from the tip of the distal end portion 24.

The illumination controller 33 controls the timing of turning on the light source 312 on the basis of an instruction signal that is input from the processing device 5. Specifically, the illumination controller 33 turns off the light source 312 in cycles of a predetermined period. The illumination controller 33 is configured by using a central processing unit (CPU) and others.

Configuration of Display Device

Next, a configuration of the display device 4 is described below.

The display device 4 displays in-vivo images that are input from the processing device 5. In addition, the display device 4 displays various types of information regarding the endoscope system 1. The display device 4 is configured by using, for example, liquid crystal or organic electro luminescence (EL).

Configuration of Processing Device

Next, a configuration of the processing device 5 is described below.

The processing device 5 includes an image acquiring unit 51, an RTS noise detecting unit 52, a recording unit 53, an image processing unit 54, and a processing controller 55.

The image acquiring unit 51 acquires the image data (RAW data) generated by the imaging element 244 disposed in the endoscope 2. Specifically, the image acquiring unit 51 sequentially acquires image data from the imaging element 244 at a predetermined frame rate under the control of the processing controller 55. In addition, the image acquiring unit 51 outputs the image data acquired from the imaging element 244 to each of the RTS noise detecting unit 52 and the image processing unit 54 under the control of the processing controller 55.

The RTS noise detecting unit 52 detects an RTS noise included in the image data (RAW data) input from the image acquiring unit 51, generates RTS noise information regarding the position (pixel address) of the pixel in which the detected RTS noise has occurred (hereinafter called a "flickering defective pixel") on the imaging element 244, and outputs the RTS noise information to the recording unit 53. The RTS noise detecting unit 52 includes a dark level determining unit 521, an accumulating unit 522, a calculating unit 523, an RTS noise determining unit 524, and an RTS noise information generating unit 525.

The dark level determining unit 521 determines, for each pixel in the image corresponding to the image data sequentially input from the image acquiring unit 51, whether the pixel value (output value) is equal to or less than a preset threshold as a dark level. The threshold as a dark level herein refers to a value obtained by multiplying a predetermined coefficient (1.2 times, for example) by the average of pixel values of individual pixels in the image corresponding to the image data generated by the imaging element 244 being in the state where the imaging element 244 is shielded from light. Needless to say, the threshold as a dark level may be the average of pixel values of individual pixels in the image corresponding to the image data generated by the imaging element 244 being in the state where the imaging element 244 is shielded from light. Furthermore, the dark level determining unit 521 may use the average value of pixels surrounding the pixel of interest (for example, eight pixels surrounding the pixel of interest) as the threshold as a dark level. In this case, when a defective pixel (a white spot or black spot) or a flickering defective pixel in the surrounding pixels is recorded in the recording unit 53, the dark level determining unit 521 may calculate the average excluding pixel values of such defective pixel and flickering defective pixel and use the average as the threshold as a dark level.

Every time the dark level determining unit 521 makes a determination, the accumulating unit 522 accumulates, for a predetermined number of frames, the pixel value that has been determined by the dark level determining unit 521 to be equal to or less than the threshold as a dark level and the positional information regarding the position of the pixel whose pixel value has been determined to be equal to or less than the threshold as a dark level, on the imaging element 244.

The calculating unit 523 calculates, for each pixel, a statistical value of pixel values accumulated in the accumulating unit 522. Specifically, the calculating unit 523 calculates, for each pixel, the standard deviation of the pixel values and the maximum width of spread in both the positive and negative directions in an output distribution of the pixel values.

The RTS noise determining unit 524 determines, for each pixel, whether an RTS noise is generated in the pixel on the basis of the statistical value calculated by the calculating unit 523 for each pixel. Specifically, the RTS noise determining unit 524 determines whether the statistical value calculated by the calculating unit 523 for each pixel falls outside a preset range, and determines that the pixel whose statistical value falls outside the range is a flickering defective pixel (an RTS noise). The preset range herein refers to either the range based on the standard deviation of pixel values of normal pixels or the maximum width of spread in both the positive and negative directions in an output distribution of pixel values of normal pixels. Specifically, the RTS noise determining unit 524 determines whether the standard deviation calculated by the calculating unit 523 for each pixel falls outside the predetermined range on the basis of the standard deviation calculated by the calculating unit 523 for each pixel, and determines that a pixel whose standard deviation falls outside the range is a flickering defective pixel, or the RTS noise determining unit 524 determines whether the maximum width of spread in both the positive and negative directions in an output distribution of the pixel values calculated by the calculating unit 523 falls outside the maximum width range of spread in both the positive and negative directions in an output distribution of pixel values of normal pixels, and determines that a pixel whose maximum width of spread in both the positive and negative directions in an output distribution of pixel values falls outside the maximum width range of spread in both the positive and negative directions in an output distribution of pixel values of normal pixels is a flickering defective pixel.

The RTS noise information generating unit 525 generates positional information regarding the position (pixel address) of the flickering defective pixel on the imaging element 244, the flickering defective pixel being determined to fall outside the range by the RTS noise determining unit 524, and the positional information being designated as RTS noise information, and outputs the RTS noise information to the recording unit 53. In this case, the RTS noise information generating unit 525 may generate the RTS noise information in which the positional information regarding the flickering defective pixel on the imaging element 244 is associated with the statistical value calculated by the calculating unit 523, and output the RTS noise information to the recording unit 53.

The recording unit 53, which is configured by using a volatile memory and/or a non-volatile memory, records various types of information regarding the endoscope system 1. The recording unit 53 includes a program recording unit 531 that records data and programs to be executed by the endoscope system 1, a white spot information recording unit 532 that records white spot information regarding the position (pixel address) of a white spot on the imaging element 244, a black spot information recording unit 533 that records black spot information regarding the position (pixel address) of a black spot on the imaging element 244, and an RTS noise information recording unit 534 that records RTS noise information generated by the RTS noise information generating unit 525.

The image processing unit 54, which is configured by using a graphics processing unit (GPU), a field programmable gate array (FPGA), or the like, performs predetermined image processing on the image data (RAW data) input from the image acquiring unit 51 and outputs the resulting data to the display device 4. Specifically, the image processing unit 54 performs processing such as demosaicing processing, white balance adjustment processing, gain adjustment processing, defective pixel correction processing, RTS noise correction processing, and format conversion processing on the image data and outputs the resulting data to the display device 4. The image processing unit 54 includes at least a pixel correcting unit 541 and an RTS noise correcting unit 542.

The pixel correcting unit 541 corrects a white spot and a black spot included in the image data, on the basis of the white spot information recorded in the white spot information recording unit 532 and the black spot information recorded in the black spot information recording unit 533. For example, the pixel correcting unit 541 corrects the pixel value of the pixel in which a white spot or a black spot is generated, by using the average of pixel values of pixels surrounding the pixel in which the white spot or black spot is generated.

The RTS noise correcting unit 542 corrects an RTS noise included in the image data, on the basis of the RTS noise information recorded in the RTS noise information recording unit 534. For example, the RTS noise correcting unit 542 corrects the pixel value of the pixel in which an RTS noise is generated, by using the average of pixel values of pixels surrounding the pixel in which the RTS noise is generated.

The processing controller 55 controls driving of the individual units included in the endoscope system 1. The processing controller 55 is configured by using a CPU and others. In addition, when an instruction signal indicating pre-freezing is input from the operating portion 22, the processing controller 55 causes the light source unit 31 to be turned off via the illumination controller 33.

Process in Endoscope System

Figure 3:
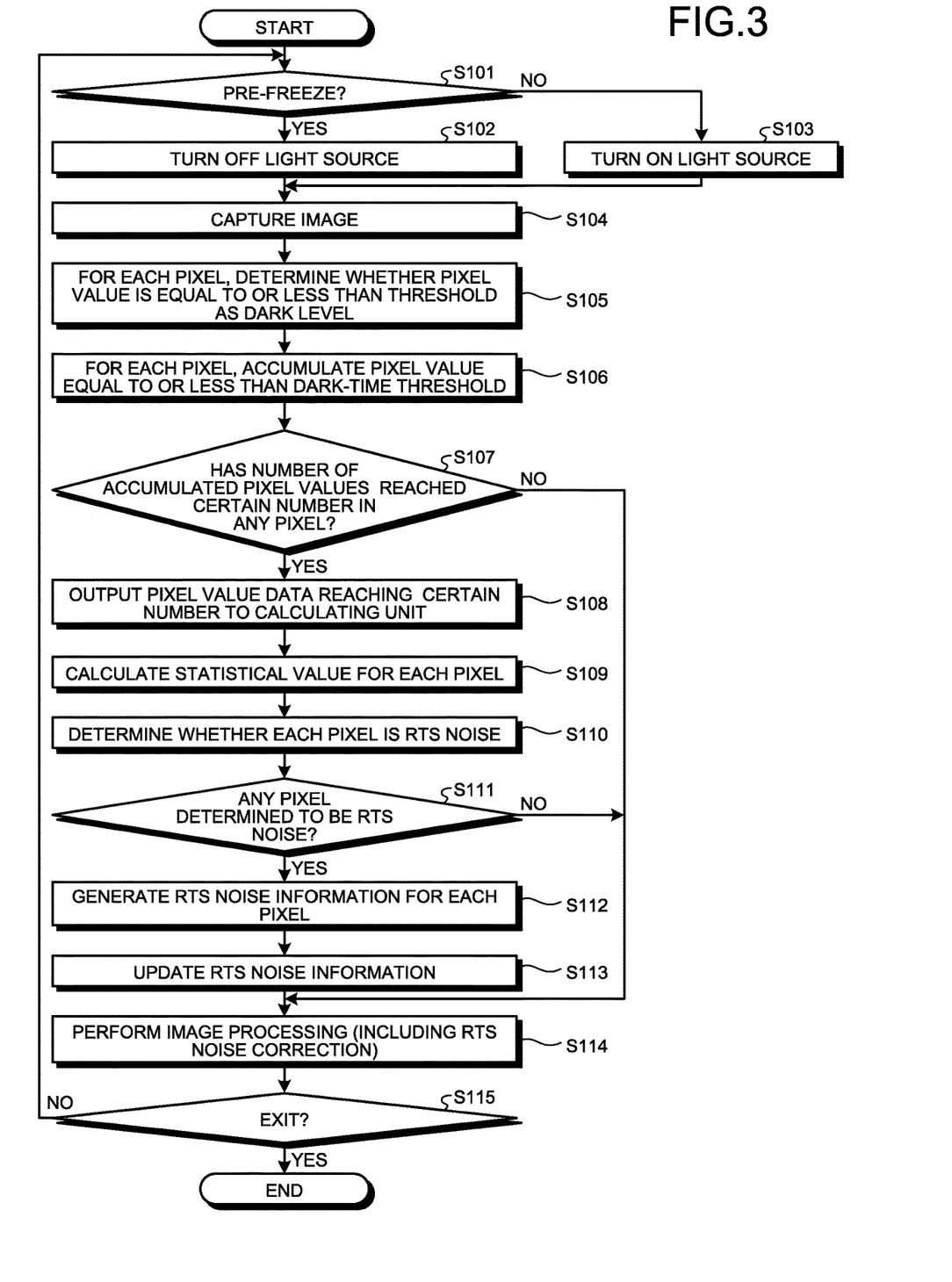
FIG. 3 is a flowchart illustrating an outline of a process performed by the endoscope system according to one embodiment of the present disclosure.

A process performed by the endoscope system 1 will now be described. FIG. 3 is a flowchart illustrating an outline of a process performed by the endoscope system 1.

First, as illustrated in FIG. 3, when an instruction signal indicating pre-freezing is input from the operating portion 22 (step S101: Yes), the processing controller 55 causes the light source unit 31 to be turned off via the illumination controller 33 (step S102). After step S102, the endoscope system 1 goes to step S104, which is described later. On the other hand, if no instruction signal indicating pre-freezing is input from the operating portion 22 (step S101: No), the processing controller 55 causes the light source unit 31 to be turned on via the illumination controller 33 (step S103). After step S103, the endoscope system 1 goes to step S104, which is described later.

In step S104, the processing controller 55 causes, via the imaging controller 246, the imaging element 244 to capture an image. In this case, the image acquiring unit 51 acquires from the imaging element 244 the image data generated by the imaging element 244. At this time, the image corresponding to the image data generated by the imaging element 244 under the condition that the light source unit 31 is turned off represents a totally dark area (a dark image) like in the state where the imaging element 244 is shielded from light. By contrast, the image corresponding to the image data generated by the imaging element 244 under the condition that the light source unit 31 is turned on represents a partly dark area (a dark image) like in the state where the imaging element 244 is partly shielded from light, because the endoscope 2 takes an intraluminal image of the subject and the reflected light of the illumination light emitted along the luminal direction (depth direction) cannot be received.

Next, the dark level determining unit 521 determines, for each pixel in the image corresponding to the image data input from the image acquiring unit 51, whether the pixel value is equal to or less than a preset threshold as a dark level (step S105).

Then, the accumulating unit 522 accumulates, for each pixel, the pixel value and positional information regarding the pixel that has been determined to have a pixel value equal to or less than the threshold as a dark level by the dark level determining unit 521 (step S106).

Then, if there is a pixel whose number of pixel values of any pixel as accumulated in the accumulating unit 522 reaches a certain number (256 or 2,000, for example) (step S107: Yes), the accumulating unit 522 outputs the pixel value data of the pixel reaching the certain number to the calculating unit 523 (step S108). After step S108, the endoscope system 1 goes to step S109, which is described later.

On the other hand, in step S107, if there is no pixel whose number of pixel values as accumulated in the accumulating unit 522 reaches the certain number (step S107: No), the endoscope system 1 goes to step S114, which is described later.

In step S109, the calculating unit 523 calculates a statistical value for each pixel that is input from the accumulating unit 522. Specifically, as the statistical value, the calculating unit 523 calculates the standard deviation of output values of each pixel and the maximum width of spread in both the positive and negative directions in an output distribution of pixel values of each pixel.

Next, the RTS noise determining unit 524 determines, for each pixel, whether an RTS noise has been generated in the pixel on the basis of the statistical value calculated by the calculating unit 523 for each pixel (step S110). Specifically, the RTS noise determining unit 524 determines whether the statistical value calculated by the calculating unit 523 for each pixel falls outside a preset range, and determines that the pixel whose statistical value falls outside the range is a flickering defective pixel (an RTS noise).

Then, if it is determined that there is a pixel that has been determined to be an RTS noise by the RTS noise determining unit 524 (step S111: Yes), the endoscope system 1 goes to step S112, which is described later. On the other hand, if it is determined that there is no pixel that has been determined to be an RTS noise by the RTS noise determining unit 524 (step S111: No), the endoscope system 1 goes to step S114, which is described later.

In step S112, the RTS noise information generating unit 525 generates positional information, designated as RTS noise information, regarding the position (pixel address) of the pixel that has been determined to be an RTS noise by the RTS noise determining unit 524, on the imaging element 244.

Next, the RTS noise information is recorded on the RTS noise information recording unit 534, whereby the RTS noise information is updated (step S113).

Then, the image processing unit 54 performs predetermined image processing on the image data in which the RTS noise has been corrected, and outputs the resulting data to the display device 4 (step S114). In this case, the RTS noise correcting unit 542 corrects the pixel value of the pixel in which an RTS noise is generated, on the basis of the RTS noise information recorded in the RTS noise information recording unit 534.

Next, if an instruction signal indicating exiting is input from the operating portion 22 (step S115: Yes), the endoscope system 1 exits the process. On the other hand, if no instruction signal indicating exiting is input from the operating portion 22 (step S115: No), the endoscope system 1 returns to step S101 described above.

According to one embodiment of the present disclosure described above, the RTS noise determining unit 524 determines whether the statistical value calculated by the calculating unit 523 for each pixel falls outside a preset range to determine that the pixel whose statistical value falls outside the range is a flickering defective pixel (an RTS noise), and the RTS noise correcting unit 542 corrects the pixel value of the flickering defective pixel in which an RTS noise is generated, on the basis of the RTS noise information generated by the RTS noise information generating unit 525. Therefore, a flickering defective pixel in the imaging element 244 can be reliably detected and corrected in real time.

According to one embodiment of the present disclosure, the RTS noise detecting unit 52, the RTS noise information recording unit 534, and the RTS noise correcting unit 542 are disposed in the processing device 5, but this is not restrictive, and the RTS noise detecting unit 52, the RTS noise information recording unit 534, and the RTS noise correcting unit 542 may be disposed in the endoscope 2. In this case, the RTS noise detecting unit 52, the RTS noise information recording unit 534, and the RTS noise correcting unit 542 can be disposed in the connector unit 27 of the endoscope 2. As a result, the image data with an RTS noise reliably detected and corrected can be output to the processing device 5 even when the type of the processing device 5 has been changed.

According to one embodiment of the present disclosure, the RTS noise detecting unit 52, the RTS noise information recording unit 534, and the RTS noise correcting unit 542 are disposed in the processing device 5, but this is not restrictive, and the RTS noise detecting unit 52 and the RTS noise information recording unit 534 may be disposed in the endoscope 2 while the RTS noise correcting unit 542 may be disposed in the processing device 5. Needless to say, only the RTS noise information recording unit 534 may be disposed in the endoscope 2, or only the RTS noise detecting unit 52 may be disposed in the endoscope 2.

Other Embodiments

In addition, one embodiment of the present disclosure has been described with a simultaneous lighting endoscope system taken as an example, but the present disclosure can also be applied to a sequential lighting endoscope system.

In addition, in one embodiment of the present disclosure, endoscope systems including a rigid endoscope, a sinus endoscope, an electric scalpel, a test probe, or the like other than flexible endoscopes (upper and lower endoscopy scopes) can also be applied.

Furthermore, one embodiment of the present disclosure has been described with an endoscope insertable into a subject taken as an example, but the present disclosure can also be applied to a capsule endoscope having the imaging element, the light source device, and the processing device disposed in a capsule-shaped casing insertable into a subject.

Furthermore, in the present disclosure, the processing controller 55 causes the light source unit 31 to be turned off so that the imaging element 244 is caused to generate image data representing the dark state; however, in another example, a rotating filter having a light-shielding region on an optical path of the light source unit 31 may be disposed, and the rotating filter may be rotated to mimic the turned-off light source unit 31 when an instruction signal indicating pre-freezing is input.

Furthermore, in the present disclosure, the RTS noise correcting unit 542 corrects a flickering defective pixel in real time; however, for example, the image data continuously generated by the imaging element 244 may be sequentially recorded on a recording medium, and a flickering defective pixel may be corrected when the image data recorded on the recording medium is played back.

Moreover, in embodiments of the present disclosure, the processing device and the light source device are separated; however, these devices may be integrally formed.

Moreover, in embodiments of the present disclosure, the "unit" mentioned above can be replaced with, for example, "means" or "circuit". For example, the image processing unit can be replaced with the image processing means or the image processing circuit.

Note that descriptions of the flowchart herein use expressions such as "first", "then", and "next" to indicate a sequential relationship among process steps; however, the sequential order of process steps necessary to carry out the present disclosure is not uniquely defined by these expressions. That is, the order of process steps in the flowchart described herein can be changed to the extent that no contradiction arises.

The present disclosure provides an effect of being capable of detecting and correcting a flickering defective pixel in an imaging element when the imaging element is in use.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A processing device comprising:
  a processor comprising hardware, the processor being configured to
  acquire image data generated by an image sensor,
  determine, for each pixel of an image corresponding to the acquired image data, whether a pixel value of the pixel is equal to or less than a preset threshold as a dark level,
  accumulate, for a predetermined number of frames, the pixel value that has been determined to be equal to or less than the preset threshold as a dark level and positional information regarding a position of the pixel whose pixel value has been determined to be equal to or less than the preset threshold as a dark level, on the image sensor,
  calculate a statistical value of the accumulated pixel values for each pixel,
  determine, for each pixel, whether the statistical value falls outside a preset range, and
  correct a pixel value of the pixel whose statistical value has been determined to fall outside the preset range.

2. The processing device according to claim 1, wherein the processor is further configured to
  generate, as RTS noise information, the positional information regarding the pixel whose statistical value has been determined to fall outside the preset range, and
  the processing device further comprises a memory configured to record the generated RTS noise information.

3. The processing device according to claim 1, wherein the statistical value is standard deviation of the accumulated pixel values for each pixel.

4. The processing device according to claim 1, wherein the statistical value is a maximum width of spread in both positive and negative directions in an output distribution of the accumulated pixel values for each pixel.

5. The processing device according to claim 1, further comprising:
  a processing controller configured to cause a light source to be turned off when an instruction signal indicating an instruction to turn off the light source is input from an operating portion of an endoscope, the light source being configured to irradiate a subject with illumination light.

6. An endoscope comprising:
  an image sensor configured to capture an image of a subject to generate image data; and
  a processor comprising hardware, the processor being configured to
  determine, for each pixel of an image corresponding to the image data generated by the image sensor, whether a pixel value of the pixel is equal to or less than a preset threshold as a dark level,
  every time a determination of the pixel value is performed, accumulate, for a predetermined number of frames, the pixel value that has been determined to be equal to or less than the preset threshold and positional information regarding a position of the pixel whose pixel value has been determined to be equal to or less than the preset threshold, on the image sensor,
  calculate a statistical value of the accumulated pixel values for each pixel,
  determine, for each pixel, whether the statistical value falls outside a preset range, and
  correct a pixel value of the pixel whose statistical value has been determined to fall outside the preset range.

7. The endoscope according to claim 6, further comprising:
  an insertion portion to be inserted into the subject; and
  a connector connectable to a processing device, wherein
  the insertion portion includes the image sensor at a distal end portion of the insertion portion, and
  the connector includes the processor.

8. An endoscope system comprising:
  an endoscope comprising an image sensor configured to capture an image of a subject to generate image data;
  a processing device configured to perform image processing on the image data; and
  a processor comprising hardware, the processor being configured to
  determine, for each pixel of an image corresponding to the image data generated by the image sensor, whether a pixel value of the pixel is equal to or less than a preset threshold as a dark level,
  every time a determination of the pixel value is performed, accumulate, for a predetermined number of frames, the pixel value that has been determined to be equal to or less than the preset threshold and positional information regarding a position of the pixel whose pixel value has been determined to be equal to or less than the preset threshold, on the image sensor,
  calculate a statistical value of the accumulated pixel values for each pixel,
  determine, for each pixel, whether the statistical value falls outside a preset range, and
  correct a pixel value of the pixel whose statistical value has been determined to fall outside the preset range.

9. An image processing method comprising:
  acquiring image data generated by an image sensor;

determining, for each pixel of an image corresponding to the acquired image data, whether a pixel value of the pixel is equal to or less than a preset threshold as a dark level;

every time a determination of the pixel value is performed, accumulating, for a predetermined number of frames, the pixel value that has been determined to be equal to or less than the preset threshold and positional information regarding a position of the pixel whose pixel value has been determined to be equal to or less than the preset threshold, on the image sensor;

calculating a statistical value of the accumulated pixel values for each pixel;

determining, for each pixel, whether the statistical value falls outside a preset range; and correcting a pixel value of the pixel whose statistical value has been determined to fall outside the preset range.

10. A non-transitory computer-readable recording medium with an executable program stored thereon, the program causing a processing device to execute:

acquiring image data generated by an image sensor;

determining, for each pixel of an image corresponding to the acquired image data, whether a pixel value of the pixel is equal to or less than a preset threshold as a dark level;

every time a determination of the pixel value is performed, accumulating, for a predetermined number of frames, the pixel value that has been determined to be equal to or less than the preset threshold and positional information regarding a position of the pixel whose pixel value has been determined to be equal to or less than the preset threshold, on the image sensor;

calculating a statistical value of the accumulated pixel value for each pixel;

determining, for each pixel, whether the statistical value falls outside a preset range; and correcting a pixel value of the pixel whose statistical value has been determined to fall outside the preset range.

* * * * *